(12) United States Patent
Matzinger

(10) Patent No.: US 7,118,916 B2
(45) Date of Patent: Oct. 10, 2006

(54) METHOD OF REDUCING ANALYSIS TIME OF ENDPOINT-TYPE REACTION PROFILES

(75) Inventor: David Matzinger, Menlo Park, CA (US)

(73) Assignee: Lifescan, Inc., Milpita, CA (US)

( * ) Notice: Subject to any disclaimer, the term of this patent is extended or adjusted under 35 U.S.C. 154(b) by 527 days.

(21) Appl. No.: 10/278,167

(22) Filed: Oct. 21, 2002

(65) Prior Publication Data

US 2004/0078149 A1    Apr. 22, 2004

(51) Int. Cl.
  *G01N 33/00* (2006.01)
  *G01N 21/01* (2006.01)

(52) U.S. Cl. .................... 436/34; 422/56; 422/58; 422/61; 422/63; 422/64; 422/65; 422/66; 422/67; 422/73; 422/82.02; 422/82.03; 422/82.05; 422/82.06; 422/82.07; 422/82.08; 422/82.09; 422/105; 422/108; 436/43; 436/46; 436/50; 436/55; 436/66; 436/69; 436/71; 436/95; 436/98; 436/108; 436/149; 436/150; 436/151; 436/164; 436/169; 436/172

(58) Field of Classification Search .................. 436/34, 436/43, 46, 50, 55, 66, 69, 71, 95, 98, 108, 436/149–151, 164, 169, 172; 422/55–58, 422/61, 63–67, 73, 82.01–82.03, 82.05–82.09, 422/105, 108
See application file for complete search history.

(56) References Cited

U.S. PATENT DOCUMENTS

| | | | |
|---|---|---|---|
| 3,769,178 A | 10/1973 | Rothermel | |
| 3,890,099 A * | 6/1975 | Jung | 436/108 |
| 4,180,440 A | 12/1979 | Gibboney et al. | |
| 4,236,894 A * | 12/1980 | Sommervold | 436/43 |
| 4,266,942 A | 5/1981 | Vandenbossche et al. | |
| 5,047,351 A * | 9/1991 | Makiuchi et al. | 436/169 |
| 5,246,858 A * | 9/1993 | Arbuckle et al. | 436/8 |
| 5,597,532 A * | 1/1997 | Connolly | 422/58 |
| 5,646,046 A * | 7/1997 | Fischer et al. | 436/49 |
| 5,780,304 A | 7/1998 | Matzinger et al. | 436/169 |
| 5,942,102 A * | 8/1999 | Hodges et al. | 205/775 |
| 6,168,957 B1 | 1/2001 | Matzinger et al. | 436/158 |
| 6,372,505 B1 | 4/2002 | Amrein et al. | |
| 6,448,067 B1 * | 9/2002 | Tajnafoi | 435/288.7 |
| 6,541,266 B1 * | 4/2003 | Modzelewski et al. | 436/95 |
| 6,885,883 B1 * | 4/2005 | Parris et al. | 600/347 |
| 2002/0146835 A1 | 10/2002 | Modzelewski et al. | |

FOREIGN PATENT DOCUMENTS

| | | |
|---|---|---|
| DE | 34 39 181 | 4/1986 |
| EP | 0 501 682 | 9/1992 |
| WO | WO 96 07908 | 3/1996 |
| WO | WO 02 40991 | 5/2002 |

OTHER PUBLICATIONS

Schwartz, L. M. et al, Analytica Chimica Acta 1983, 155, 67-77.*
"Metrohm Programm 1996, Uebersichtskatalog" Metrohm, XX, XX 1989, pp. 6, 12, XP002148799.

(Continued)

*Primary Examiner*—Arlen Soderquist
(74) *Attorney, Agent, or Firm*—Kagan Binder PLLC

(57) ABSTRACT

Methods, devices and kits for facilitating medical diagnostic assays and reducing the time required for taking of such assays. The methods comprise initiating a reaction, obtaining at least three measurements, at three different time points, of a value or level of an observable associated with the reaction, and estimating an end point value for the observable from the measurements.

18 Claims, 3 Drawing Sheets

OTHER PUBLICATIONS

Patent Abstracts of Japan, vol. 013, No. 357 (P-915) Aug. 10, 1989, JP 01 116447 A (Ebara Infilco Co LTD;OTHERS:01) May 9, 1989.

"Prospekt Der Firma Mettler ME-724171" Prospekt Mettler Instrumente, XX, XX, 1989, pp. 1-8, XP002148799.

* cited by examiner

US 7,118,916 B2

METHOD OF REDUCING ANALYSIS TIME OF ENDPOINT-TYPE REACTION PROFILES

BACKGROUND OF THE INVENTION

In the field of clinical chemistry, diagnostic analyses often consist of chemical reactions in which an analyte is reacted to form an observable product at a rate proportional to the amount of analyte still present in the reaction. This is referred to as a first order reaction, wherein the rate of product formation is proportional to the first order of the reactant, i.e., the analyte. First order kinetic reactions produce an exponential concentration vs. time profile that is modeled mathematically by an exponential equation wherein an observable response proportional to the concentration of the reaction product is related to reaction time and a reaction rate constant. The observable response may be, for example, a colorimetric determination of the concentration of a reactant or a reaction product. The rate constant of the reaction is typically variable with temperature and usually increases with increasing temperature.

Situations are frequently encountered where reaction profiles are not strictly first order, but are close enough to be approximated by a first order kinetics exponential through much of the reaction's time course. This is often the case with enzymatically catalyzed reactions where the reaction rate (at a given temperature) is a function of both enzyme and analyte (reactant) concentration. Characterization of the reaction end point usually requires that the reaction be carried to completion. The reaction may in some instances be speeded up by increasing either temperature or enzyme or other catalyst concentration. However, in many cases a reaction must be carried out at ambient temperature, and even with increasing the enzyme or catalyst concentration, the time needed to reach a limiting observable response may require long endpoint times.

Many medical diagnostic tests for reactions of first order or pseudo-first order kinetics are based on end point assays that are carried out under ambient temperature conditions. Most such assays require that the amount of time allowed for reaction be sufficient to obtain a reproducible value for an observable response associated with the end point of the reaction. Assays for the detection of chemical and biochemical compounds may thus take minutes or hours to obtain a reasonably accurate observed response or value that is indicative of the reaction end point.

The wait time required to obtain a reaction end-point for many clinical and biochemical assays can reduce the productivity of medical laboratories and may have unacceptably long endpoint times in emergency situations. Further, many commonly used assays, such as blood glucose level tests for diabetics and thromboplastin-based tests for anticoagulation patients, are increasingly performed by lay persons in non-clinical settings. Lack of skill or patience in making measurements over the necessary time period by such lay persons can require inconvenient repetition of test measurements, increase the risk of obtaining erroneous diagnostic data, and can ultimately lead to non-optimal clinical outcomes associated with test measurements that are improperly carried out.

There is accordingly a need for methods that reduce the overall assay time for medical diagnostic tests, and which facilitate and simplify such tests. The present invention satisfies these needs, as well as others, and generally overcomes the deficiencies found in the background art.

SUMMARY OF THE INVENTION

The invention provides methods for facilitating medical diagnostic assays and reducing the time required for taking of such assays. More specifically, the invention provides methods for determining solutions to a first order reaction kinetics exponential from measurements taken at different time intervals that allow a computational estimate of a reaction end point to be made. The invention also provides methods for approximating a first order reaction from measurements taken at different time intervals. The methods comprise, in general terms, initiating a reaction, obtaining at least three measurements, at three different time points, of a value or level associated with observable species indicative of the reaction, and estimating an end point value for the observable species from the measurements. The end point value may be estimated according to the difference of an intermediate measured value, less a number equal approximately to the square of the difference between a later measured and an earlier measured value divided by a number equal approximately to an integer multiple of the later measured value less twice the intermediate measured value plus the initial measured value.

By way of example, and not of limitation, the reaction may comprise any chemical, biological, physiological or other reaction having first order or pseudo-first order behavior or characteristics. The observable species associated with the reaction may comprise a molecule or molecules, or a label or labels associated therewith, that are detectable optically, electrically, spectroscopically, radiologically, chemically, or via other technique, which may be embodied in a sample meter, sample reader or other detection device. The observable species may comprise a detectable analyte or reactant in the reaction, a detectable reaction product, or a detectable species, compound or chemical that does not participate in the reaction but which is indicative of the concentration or level of reagent or analyte in the reaction. The measurements of values may, in many embodiments, be taken or obtained at equal or substantially equal time intervals $\Delta t$. In other embodiments, differing time intervals may separate individual measurements. The taking of measurements may occur early or late in the reaction, or both. The methods may further comprise determining an end point time for the reaction from the measurements.

The subject methods may, in certain embodiments, comprise initiating a reaction in which an observable species A is indicative of the extent of reaction is present, measuring first, second and third values $A_1$, $A_2$, and $A_3$ for the observable species, and determining a final or endpoint value $A_\infty$ for the observable species according to according to the relationship $$A_\infty \cong A_2 - \frac{(A_3 - A_1)^2}{4(A_3 - 2A_2 + A_1)}.$$

The measurements of values $A_1$, $A_2$, and $A_3$ may be taken at equal or substantially equal time intervals $\Delta t$ in many embodiments, while in certain embodiments the measurements of values $A_1$, $A_2$, and $A_3$ may be made at intervals of unequal duration, and measurements may be specifically made after selected durations. The measurements of values $A_1$, $A_2$, and/or $A_3$ may be made or initiated generally at any time after initiation of the reaction, and determination of the end point value does not require characterization or noting of the reaction initiation time. In some embodiments, measurement of values $A_1$, $A_2$, and/or $A_3$ may be carried out after a selected amount of time has elapsed after initiation of the reaction, or after a selected amount of time after a previously taken measurement or measurements.

The methods of the invention may in some embodiments comprise measuring a first set of values of $A_1$, $A_2$, and $A_3$ for the observable species during a first observation window and determining a first end point value $A_\infty$ according to the above relationship, measuring a second set of values of $A_1$, $A_2$, and $A_3$ of the observable species during a second, subsequent observation window and determining a second end point value $A_\infty$, and determining a difference in end point value $\Delta A_\infty$ from the first and second endpoint values. The methods may further comprise measuring an nth set of values $A_1$, $A_2$, and $A_3$ for the observable species during an nth observation window, determining an nth end point value $A_\infty$, determining values of $\Delta A_\infty$ from the first, second and nth sets of values, and selecting a time interval after reaction initiation for an observation window for measuring values $A_1$, $A_2$, and $A_3$ of the observable species.

The measurement of a set of values $A_1$, $A_2$, and $A_3$ during a reaction can be considered as an "observation window" on the reaction of interest, during which the three measurements of values $A_1$, $A_2$, and $A_3$ are made. The observation window is movable in time with respect to the reaction initiation, and is repeatable to provide successive estimates of the endpoint value $A_\infty$. The inherent systematic error in the estimate of the endpoint value $A_\infty$ is a constant percentage of $A_\infty - A_2$ for any given time interval $\Delta t$ between individual measurements, and for any given reaction constant k. The error as a percentage of the desired result $A_\infty$ becomes smaller as the "three observation window" progresses in time, leading to more accurate estimates of $A_\infty$ at later times during the reaction.

The percent error in the estimation of the endpoint value $A_\infty$ thus is a function of the time interval $\Delta t$ between measurement of values $A_1$, $A_2$, and $A_3$, the degree of completion of the reaction, and the reaction constant k. To insure that the error of the estimate of $A_\infty$ is within an acceptable amount of the true or actual value, these parameters may be adjusted by ensuring that the reaction has proceeded beyond a certain degree of completion, prior to taking measurements, by comparing measured values $A_t$ to the estimate of the end point value $A_\infty$, optimizing the time interval $\Delta t$ between measurements for the observed reaction constant k, and/or by observing temperature during the reaction and applying a known relationship between temperature and reaction constant k. At higher temperatures, (higher values of k), $\Delta t$ may be smaller to compensate for greater curvature in a time curve for measured values A of the observable species, while at very low values of k, small differences between successive values of A lead to poor signal to noise ratios in the presence of random error. Thus, in many embodiments the time interval $\Delta t$ should be as large as possible at a given reaction constant k, within the constraints of the allowable error at the desired minimum degree of completion.

Background noise is an important factor in many detection systems for measuring values of observable species associated with a reaction. It is thus desirable in some embodiments of the invention to examine multiple, successive estimates of the endpoint value $A_\infty$ to check for convergence, which gives both an indication of degree of completion as well as the signal to noise ratio present during measurements. Also, since the systematic error is a constant fraction of an exponential, the change of the estimate with time is itself an exponential for which and estimate of the endpoint value could also be projected to further reduce systematic error.

The subject methods reduce the overall assay time necessary for endpoint determination in medical, biological and other assays. The reduced time requirement for assays leads to greater convenience for users and more efficient use of medical laboratory personnel and resources. The invention also allows for the estimation of an endpoint of an exponential reaction without using logs or exponentials, such that the calculation required for endpoint estimation can easily be carried out with low-power microprocessors such as those available in metering or reader devices and hand held data processors such as "personal digital assistant" or PDA devices. The invention further allows for end point estimation without knowing the precise starting time of an assay reaction.

The invention is usable with numerous diagnostic tests including, for example, determining patient exposure to and uptake of therapeutic drugs, determining the level of intoxicants present in individuals, and detecting the possible presence of hazardous chemicals in samples. The methods of the invention are particularly useful for medical diagnostic tests such as blood glucose monitoring and monitoring of anticoagulant therapies, which are commonly carried out in the "field" or outside of clinical settings by patients and lay persons. These and other objects and advantages of the invention will be apparent from the detailed description below.

BRIEF DESCRIPTIONS OF THE DRAWINGS

The present invention will be more fully understood by reference to the following drawings, which are for illustrative purposes only.

DETAILED DESCRIPTION OF THE INVENTION

Figure 1:
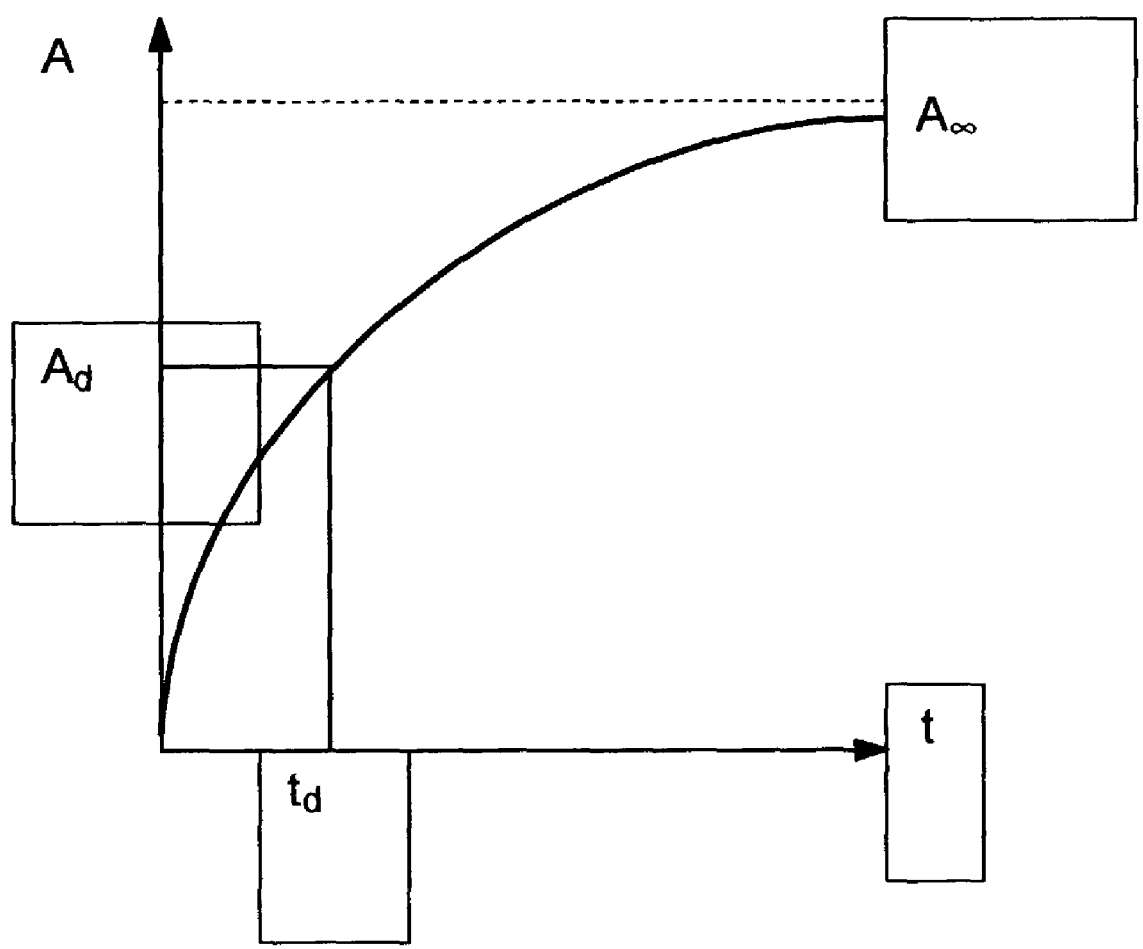
FIG. 1 is a graphical representation of a reaction with first order kinetics, with measured or observed analyte level shown on the vertical axis, and with reaction time shown on the horizontal axis.

Disclosed herein are methods for reducing assay times necessary for endpoint determination in medical biological assays. Particularly, that invention provides methods for estimation of the end point value of an observable feature or features of the reaction from three measured values of the observable that are obtained prior to the reaction end point. The invention is described primarily in terms of use with clinical or medical diagnostic assays, and blood glucose level assays in particular. Before the subject invention is described further, it should be understood that the invention is not limited to the particular embodiments described below, as variations of the particular embodiments may be made and still fall within the scope of the appended claims. It is also to be understood that the terminology employed is for the purpose of describing particular embodiments, and is not intended to be limiting. Instead, the scope of the present invention will be established by the appended claims.

Any definitions herein are provided for reason of clarity, and should not be considered as limiting. The technical and scientific terms used herein are intended to have the same meaning as commonly understood by one of ordinary skill in the art to which the invention pertains.

The term "first order reaction" as used herein means any chemical, electrochemical, biochemical or other reaction having or exhibiting first order or pseudo-first order reaction kinetics, or which can otherwise be reasonably characterized by approximation to first order reaction kinetics.

The term "prothrombin time" or "PT" and grammatical equivalents thereof as used herein means tests for blood coagulation time that are usable to monitor treatment of individuals who are at risk of excessive blood clotting (thrombosis).

The term "calibration code" and grammatical equivalents thereof as used herein means a unique number or set of numbers used for standardization of commercial lots of diagnostic assays and/or components thereof.

The term "plasma" and grammatical equivalents thereof as used herein means blood plasma, i.e., the acellular fluid in which blood cells are suspended.

The term "host", "patient", "individual" and "subject" and grammatical equivalents thereof as used herein means a member or members of any mammalian or non-mammalian species that may utilize or be in need of using the subject methods for estimation of end point values for observable features of reaction.

It should be noted that, as used in this specification and the appended claims, the singular forms "a," "an" and "the" include plural referents unless the content clearly dictates otherwise. Thus, for example, reference to "a control mixture" includes one or more such control mixtures, and "a coagulation test" includes one or coagulation tests, and the like.

In chemical and biological assays or like reaction events, an analyte is typically reacted in a manner that changes the level or value of an observable species that is proportional to the amount of analyte still present in a reaction vessel. The observable species may comprise the analyte itself, which decreases in concentration during the reaction, a reaction product that increases as the analyte is depleted, or another species that does not actually participate in the reaction, but is indicative of reaction progress. For first order reactions, the analyte reacts in an observable manner at a rate that is proportional to the amount of analyte remaining in the reaction. In monitoring the responses of such chemical reactions, the response or progress of the reaction over time may be exponential, and produce a concentration (of observable species) versus time that may be represented by the exponential equation $$A_t = A_\infty (1 - e^{-kt}) \tag{1a}$$

for the situation in which the appearance of a reaction product is being monitored, or $$A_t = (A_0 - A_\infty) e^{-kt} + A_\infty \tag{1b}$$

for the situation in which the disappearance of a reactant is being monitored, where $A_t$ is an observable response at time t, $A_\infty$ being the observable response at reaction completion, and $A_0$ being the observable response before initiation of the reaction. Another possible situation involving the disappearance of reactant would be:

$$A_t = A_0 e^{-kt} \tag{1c}$$

Equation 1a generally pertains to situations where none of the observable reaction product exists at the beginning of the reaction, and its final concentration, detected as $A_\infty$, is related to the amount of analyte (starting material) being quantitated in the diagnostic method. Equation 1b pertains to situations where a detectable starting material reacts with the analyte to form an undetectable product. The detectable starting material is present in excess, and the difference between the starting and final detectable responses ($A_0$ and $A_\infty$) is related to the amount of analyte present. Equation 1c pertains to situations where the detectable response is the analyte itself, and the response goes to zero when the reaction is complete. This invention is relevant to equations 1a and 1b. The parameter k is the rate constant of the reaction and is typically variable with temperature, usually increasing with increasing temperature. The observable response may comprise, for example, a detectable color associated with a reagent, a reaction end product, or other compound or species present in the reaction.

Many important assays, such as those used in blood glucose monitoring and monitoring of therapeutic levels of anticoagulation therapeutics, require determination of the end point value $A_\infty$. In many instances it is inconvenient to actually wait until the reaction is essentially complete to obtain an estimate $A_\infty$. In some circumstances the reaction curve predictably obeys the first order kinetic exponential mathematical form of equations (1) above, and one can solve for the parameters of the equation (k and $A_\infty$) after measuring A at a number of time points, without having to wait for the reaction to reach completion to obtain a reasonable estimate $A_\infty$. However, many reactions involved in important medical and biological assays do not follow first order reaction behavior, and reasonable estimates of $A_\infty$ cannot be easily obtained. It is also possible to carry out numerical evaluations for the parameters k and $A_\infty$ by a derivative process. This approach, however, is computationally intensive and not well suited for conventional measuring devices with limited memory and long microprocessor cycle times.

This invention provides quick, easy and accurate methods for estimation of the observable end point value $A_\infty$ that may be used with numerous biological and medical assays, as well as devices and kits for carrying out the subject methods. The methods comprise initiating a reaction in which an observable species A is present that indicative of the extent or progress of the reaction, measuring first, second and third values $A_1$, $A_2$, and $A_3$ for or the observable species at first, second and third time points $t_1$, $t_2$ and $t_3$, and determining a final or endpoint value $A_\infty$ for the observable species from the values $A_1$, $A_2$, and $A_3$ according to the relationship $$A_\infty \cong A_2 - \frac{(A_3 - A_1)^2}{4(A_3 - 2A_2 + A_1)} \tag{2}$$

The measurements of values $A_1$, $A_2$, and $A_3$ are, in many embodiments, taken at equal or substantially equal time intervals $\Delta t$, wherein $\Delta t$ is the interval between the time points of successive measurements, i.e., $\Delta t \approx t_3 - t_2 \approx t_2 - t_1$. The measurement of $A_1$, and hence $A_2$, and $A_3$, may be made or initiated generally at any time after initiation of the reaction, although measurement of values $A_1$, $A_2$, and/or $A_3$ may be carried out after a selected amount of time has elapsed after initiation of the reaction, as described further below.

The value of $\Delta t$ may be selected according to the particular reaction involved. A study of the reaction of interest at different temperatures (and hence different k values as discussed below). In this manner, when the reaction is carried out at a specific temperature or within a specific temperature range, an adequate amount of reduction in reaction time is obtained (i.e., earlier endpoints), while maintaining acceptable accuracy in the end point value $A_\infty$. This accuracy can be degraded by having $\Delta t$ too large for the amount of curvature in the reaction profile. Study of the reaction of interest at different temperatures to determine f $\Delta t$ values which are optimal for each temperature or k may employ creation of a table or other relationship, so that when the reaction is run, the best $\Delta t$ can be selected for processing the data stream used for end point determination. Temperature can be measured (via temperature sensor, thermometer or other means) or, alternatively, initial estimates of k can be made by using an arbitrarily small $\Delta t$, to process early data and approximate k values using equation (20) as discussed below.

For equation (1b), where $A_t = A_0 e^{-kt}$, plotting the log of the observable value ($\ln A_t$) vs. time yields the reaction constant k and end point value $A_\infty$ as slope and intercept, respectively; At least two measurements of A, at two different time points, would be required for this type of analysis. For $A_t = A_\infty(1 - e^{-kt})$, however, determination of reaction constant k and end point value $A_\infty$ is more complex. The effectiveness of the algorithm of equation (2) for accurate estimation of an end point observable value $A_\infty$ can be seen as follows. First, consider the differential equation (3)

$$\frac{dA}{dt} = -A_\infty k e^{-kt} \tag{3}$$

For slopes of A versus t measured at two time points, $t_1$ and $t_2$, the relationship $$\frac{\left(\frac{dA}{dt}\right)_{t1}}{\left(\frac{dA}{dt}\right)_{t2}} = \frac{A_\infty k e^{-kt_1}}{A_\infty k e^{-kt_2}} = e^{-k(t_1 - t_2)} \tag{4}$$

of equation (4) is achieved. The relationship of equation (4) can be shown more simply by $$\ln\left[\frac{\left(\frac{dA}{dt}\right)_{t1}}{\left(\frac{dA}{dt}\right)_{t2}}\right] = -k(t_2 - t_1) \tag{5}$$

Equation (5) can then be shown, in solving for the rate constant k, as $$k = -\frac{\ln\left[\frac{\left(\frac{dA}{dt}\right)_{t1}}{\left(\frac{dA}{dt}\right)_{t2}}\right]}{(t_2 - t_1)} \tag{6}$$

Substituting equation (6) into equation (1) then gives $$A_\infty = \frac{A_{t_1}}{(1 - e^{-kt_1})}. \tag{7}$$

In order to determine $A_\infty$ according to equation (7), a minimum of three measurements of values for $A_t$ would be required. Both logarithmic and exponential computations would be involved, and the solution would computationally intensive, requiring more time and computer overhead than is convenient for the low-power microprocessors commonly used in clinical assays.

However, if one goes one step further, and calculates the second derivative shown in equation (8), the situation becomes simpler.

$$\frac{d^2 A}{dt} = -A_\infty k^2 e^{-kt} \tag{8}$$

Dividing the second derivative shown in equation (8) by the first derivative dA/dt, one arrives at $$\frac{\frac{d^2 A}{dt}}{\frac{dA}{dt}} = \frac{A_\infty k^2 e^{-kt}}{A_\infty k e^{-kt}} = k \tag{9}$$

equation (9) as a solution for the rate constant k.

The graph of FIG. 1 illustrates an exponential reaction curve of measured value A versus time. FIG. 1 is illustrative of the situation wherein the starting time of a reaction of interest is not known, i.e., $t_0$ is unknown, as is frequently the case in home-use diagnostic assays used by patients. The first measurement of the observable quantity $A_d$ is taken at time $t_d$, which occurs after the unknown reaction starting time $t_0$. The relationship of equation (1) can then be expressed as $$A = A_\infty(1 - e^{-kt}) = (A_\infty - A_d)(1 - e^{-k(t - t_d)}) + A_d \tag{10}$$

The derivative of equation (10) may be shown as $$\frac{dA}{dt} = A_\infty k e^{-kt} = (A_\infty - A_d) k e^{-k(t - t_d)}, \tag{11}$$

and equation (11) can be expressed as $$A_\infty = \frac{\frac{dA}{dt}}{k e^{-k(t - t_d)}} + A_d. \tag{12}$$

For $t = t_d$, equation (12) can be simplified to $$A_\infty = \frac{\frac{dA}{dt}}{k} + A_d. \tag{13}$$

From equation (13), it can be seen that all that is needed to calculate the endpoint value $A_\infty$ are the first and second derivatives of a single point along the reaction curve of A versus time.

Figure 2:
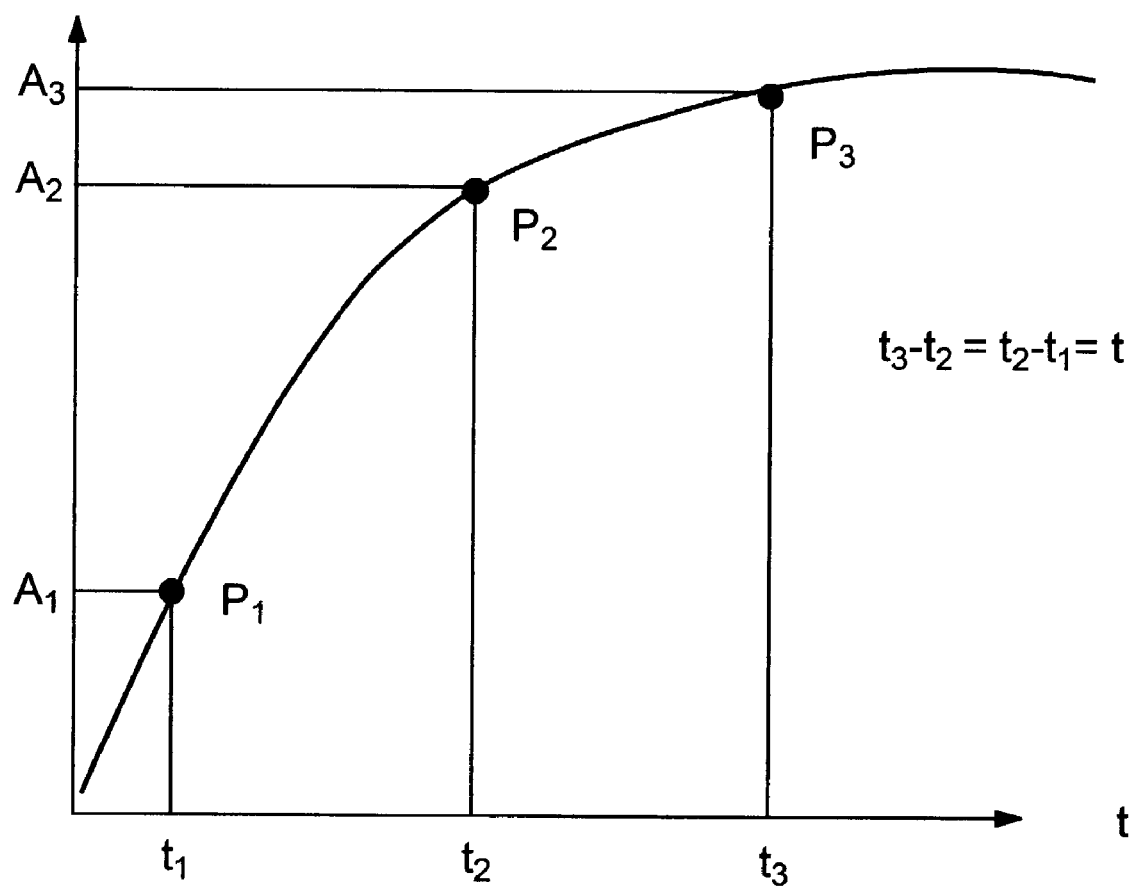
FIG. 2 is a graphical representation of a three point observation window in a reaction with first order kinetics, with measured or observed analyte level shown on the vertical axis, and with reaction time shown on the horizontal axis.

Referring now to FIG. 2, there is shown graphically a reaction curve with three points $P_1$, $P_2$ and $P_3$ on the curve, corresponding respectively to measured values $A_1$, $A_2$, and $A_3$ at time points $t_1$, $t_2$ and $t_3$, with $t_3-t_2=t_2-t_1=\Delta t$. Assume, for ex here, that the first and second derivative are assigned to point $P_2$. The slope $S_1$ of the curve of FIG. 2, which is the first derivative at a point (not shown) located midway on the curve between points $P_1$ and $P_2$, can be shown as $$S_1 = \frac{A_2 - A_1}{\Delta t}. \tag{14}$$

The slope $S_2$ of the curve of FIG. 2, taken as the first derivative at a point (not shown) located midway on the curve between points $P_2$ and $P_3$, can similarly be shown as $$S_2 = \frac{A_3 - A_2}{\Delta t}. \tag{15}$$

$S_3$, the average of the first derivatives assigned to $P_2$, can then be related as $$S_3 = \frac{S_1 + S_2}{2}, \tag{16}$$

and S', the second derivatives assigned to $P_2$, can be shown as $$S' = \frac{S_2 - S_1}{\Delta t}. \tag{17}$$

Estimating the reaction constant k from equation (9) above provides $$k \approx \frac{-S'}{S_3}, \tag{18}$$

and estimating $A_\infty$ from equation (13) above yields $$A_\infty \approx \frac{S_3}{\left(\frac{S'}{S_3}\right)} + A_2. \tag{19}$$

Solving for $A_\infty$ in terms of the measured values $A_1$, $A_2$ and $A_3$ gives equation (2), which is usable for characterization of reaction end points in accordance with the invention.

$$A_\infty \cong A_2 - \frac{(A_3 - A_1)^2}{4(A_3 - 2A_2 + A_1)} \tag{2}$$

In a similar fashion, an approximation of k can be derived:

$$k \cong \frac{A_3 - 2A_2 + A_1}{2\Delta t(A_3 - A_1)} \tag{20}$$

It should be noted that there is some error inherent in the approximation of equation (2) due to the finite nature of aforementioned the slope calculations.

Estimation of an end point value $A_\infty$ of an observable quantity A that is indicative of reaction progress or completion, thus may comprise initiating a reaction involving the observable species A, measuring first, second and third values or levels $A_1$, $A_2$, and $A_3$ for the observable species, and determining a final or endpoint value $A_\infty$ for the observable species according to according to the relationship provided in equation (2). The three successive measured values $A_1$, $A_2$ and $A_3$ can be considered as a "three observation window" which can moved in time, providing successive estimates of $A_\infty$. The inherent systematic error in the estimate is a constant percentage of $A_\infty-A_2$ for any given values of $\Delta t=t_1-t_2=t_2-t_3$) and k, so the error as a percentage of the desired result, $A_\infty$, becomes smaller as the "three observation window" progresses in time (towards the reaction end point, leading to more accurate estimates of $A_\infty$ at later times during the reaction. Thus, the percent error is a function of $\Delta t$, the degree of completion of the reaction, and k.

To insure that the error of the estimate of $A_\infty$ is less than a desired fraction of the true, value, one can fix these parameters by making sure that the reaction has progressed beyond a certain degree of completion by comparing measured values $A_t$ to the estimate of $A_\infty$, optimizing $\Delta t$ for either the observed k (which is estimatable according to equation 20), and/or by observing temperature and applying a known relationship between temperature and reaction constant k. For typical chemical reactions, at higher temperatures, k increases, so $\Delta t$ should be smaller to compensate for greater curvature, while at lower temperatures, and hence lower values of k, small differences between successive values of $A_t$ may lead to poor signal to noise ratios in the presence of random instrumental or other error. Thus, $\Delta t$ should preferably be as large as possible at a given k, within the constraints of the allowable error at the desired minimum degree of completion.

Since background noise may be an important factor in many situations that utilize the invention, it may also be desirable to examine successive estimates of $A_\infty$ to check for convergence, giving both an indication of degree of completion and signal to noise. In this regard, the methods of the invention provide for such successive estimates, by measuring a first set of values of $A_1$, $A_2$, and $A_3$ for the observable species during a first observation window and determining a first end point value $A_\infty$ according to the relationship of equation (2), measuring a second set of values of $A_1$, $A_2$, and $A_3$ of the observable species during a second, subsequent observation window and determining a second end point value $A_\infty$, and determining a difference in end point value $\Delta A_\infty$ from the first and second endpoint values. The methods may further comprise measuring a third set of values of $A_1$, $A_2$, and $A_3$ during a third observation window and determining a third end point value $A_\infty$, and measuring an nth set of values $A_1$, $A_2$, and $A_3$ during an nth observation window, determining an nth end point value $A_\infty$, and determining values of $\Delta A_\infty$ from the first, second, third and nth sets of values. The selecting of a minimum time interval, or an optimum time interval, after reaction initiation, for an observation window for measuring values $A_1$, $A_2$, and $A_3$, can thus be determined by comparison of the successive estimates of $A_\infty$ and observation of convergence of the measured value for $A_\infty$ from the different observation windows. Additionally, since the systematic error is a constant fraction of an exponential, the change of the estimate with time is itself an exponential for which and estimate of the endpoint value $A_\infty$ could also be projected to further reduce systematic error.

GENERAL METHODOLOGIES

The invention provides methods for facilitating medical diagnostic assays and reducing the time required for such assays, from measurements taken at different time intervals that allow a computational estimate of a reaction end point to be made. The methods comprise, in general terms, initiating a reaction, obtaining at least three measurements, at three different time points, of a value associated with observable species indicative of the reaction, and estimating an end point value for the observable species from the measurements. The end point value may be estimated according to the difference of an intermediate measured value, less a number equal approximately to the square of the difference between a later measured and an earlier measured value divided by a number equal approximately to an integer multiple of the later measured value less twice the intermediate measured value plus the initial measured value.

More specifically, subject methods may comprise initiating a reaction in which an observable species A is indicative of the extent of reaction, measuring first, second and third values $A_1$, $A_2$, and $A_3$ for the observable species, and determining a final or endpoint value $A_\infty$ for the observable species according to according to the relationship of equation (2) as described above $$A_\infty \cong A_2 - \frac{(A_3 - A_1)^2}{4(A_3 - 2A_2 + A_1)}. \quad (2)$$

The measurements of values $A_1$, $A_2$, and $A_3$ may be taken at equal or substantially equal time intervals $\Delta t$ in many embodiments as shown in the following examples. The measurements of values $A_1$, $A_2$, and/or $A_3$ may be made or initiated generally at any time after initiation of the reaction, or in some embodiments, measurement of values $A_1$, $A_2$, and/or $A_3$ may be carried out after a selected amount of time has elapsed after initiation of the reaction, or after a selected amount of time after a previously taken measurement or measurements.

The methods of the invention are usable with any chemical, biological, physiological or other reaction. The observable species associated with the reaction may comprise a molecule or molecules, or a label or labels associated therewith, that are detectable optically, electrically, spectroscopically, radiologically, chemically, or via other technique. The methods of the invention in particular are well suited for use with sample meters, sample readers or other detection devices having limited computing power. The observable species may comprise a detectable analyte or reactant in the reaction, a detectable reaction product, or a detectable species, compound or chemical that does not participate in the reaction but which is indicative of the concentration or level of reagent or analyte in the reaction. The specific examples discussed below utilize optically detectable compounds.

In many instances, diagnostic assay reactions which are carried out with hand held devices use a solid support such as a test pad or strip which is impregnated with a color forming reagent system specific to an analyte of interest. Typical analytes are glucose, cholesterol, urea, and the like. Many others analytes commonly involved in such diagnostic assays will readily suggest themselves to those skilled in the art. The color forming reagent system may include an enzyme or other catalyst, which selectively catalyzes a primary reaction with the analyte of interest. A product of the primary reaction may be a dye or other compound that undergoes an optically detectable change, such as a change in color that is detectable at the reaction zone. In other embodiments, the product of the primary reaction may be an intermediate which undergoes another reaction, and which may also enzyme catalyzed, and participates in a secondary reaction that, directly or indirectly, causes a final dye to undergo a change in color, which is detectable at the reaction zone.

An exemplary color-forming reagent system usable with the invention is the system that is specific to glucose and contains glucose oxidase, a peroxidase, and an oxidizable dye. Glucose oxidase is an enzyme, obtained from *Aspergillus Niger* or Penicillium, that reacts with glucose and oxygen to produce gluconolactone and hydrogen peroxide. The hydrogen peroxide so produced, catalyzed by a peroxidase enzyme, such as horseradish peroxidase, oxidizes a dye. The resulting chromophore (the oxidized dye) exhibits a color that may be observed at the reaction zone. The observable values in such embodiments would thus comprise calorimetric determinations of the level of dye present in the reaction zone.

Many suitable oxidizable dyes are known in the art for use in glucose assays including, for example, those set out in U.S. Pat. No. 5,304,468 incorporated herein by reference. Another particularly useful oxidizable dye is the 3-methyl-2-benzothiazolinone hydrazone hydrochloride/8-anilino 1-naphthalenesulfonate dye system (MBTH/ANS) described in U.S. Pat. No. 6,218,571, the disclosure of which is also incorporated herein by reference. Another dye couple of choice is a derivative of MBTH, meta-3-methyl 2-benzothiazolinone hydrazone, N-sulfonyl benzenesulfonate monosodium coupled with ANS. This combination is described in detail in U.S. patent application Ser. No. 08/302,575, filed Sep. 8, 1994 and incorporated herein by reference. Other suitable dyes and dye systems that allow optical characterization of reactions will suggest themselves to those skilled in the art.

The oxidizable dye may be used in a test strip and optical reader system such as those that are commonly employed for measurement of blood glucose levels. U.S. Pat. No. 6,268,162, for example, discloses a system for measuring analyte concentration in bodily fluids based on reflectance readings from a porous test strip, and is incorporated herein by reference. In this system, a bodily fluid sample is applied to the test strip, and the strip is then inserted into an optical reader or meter. The measured values A in this case are measured reflectance values from the test strip, and a reflectance value that corresponds to the reaction end point may be calculated from the measured reflectance values in accordance with the invention.

The measurement of values for end point estimation in accordance with the invention may also be based on electrochemical assays. Such assays may utilize test samples in an electrical cell having electrodes therein separated by a gap. Application of current across the gap while monitoring potential difference across the electrodes allows characterization of the reaction. The measured values A thus comprise measured potential values, which are used to calculate an end point potential value across the electrodes. Such a system is described in U.S. Pat. No. 6,193,873, the disclosure of which is incorporated herein by reference.

The invention may also be utilized for end point characterization of blood coagulation assays such as prothrombin time or PT assays. Such assays may be carried out by application of a blood sample to a test strip containing thromboplastin, together with optical monitoring of coagulation (via optical transmission or reflectance) using a strip reader. Such as system is disclosed in European Patent Application EP 0 974,840, which is incorporated herein by reference. Test strips of this type are commercially available from Lifescan Inc., Milpitas, Calif. A as HARMONY™ test strips, as well as the corresponding optical reader for the strips.

DEVICES

The invention also provides devices and systems useful in diagnostic assays. The devices may comprise, for example, a data processing device having an interface capable of reading, inputting or otherwise allowing entry of measured values A of an observable associated with a reaction, and a logic element or elements that is capable of employing the entered values with the algorithm shown in equation (2) and discussed above, to provide an end point value. The devices may additionally comprise a time keeping element that allows determination of time intervals between the measurements of values A, so that values may be measured at selected time intervals as described above.

The interface may comprise a user interface that allows a user to enter, via keypad or other conventional means, the measured values A. The interface may additionally, or alternatively, comprise an interface that is capable of measuring the values of A directly. Such an interface may comprise, for example, an optical reader for measuring values of A colorimetrically from test strips or other samples, circuitry for measurement of A from according to capacitance changes in samples, or other interface capable of acquiring measured values in accordance with the invention. Exemplary sample readers having such interfaces are noted above.

The logic of the subject devices may be embodied in hardware, software, or both. End point characterization in accordance with the invention does not require logarithmic or exponential characterization as noted above, and thus the data processing capability required for the subject devices is small, and may be embodied in relatively simple sample readers. The logic may, for example, be configured to read or input a plurality of measured values, apply the algorithm of equation (2) to the measured values, and output one or more end point estimation values according to the inputted measured values. The logic may further be configured to selectively time the measuring of values from a sample, and compare successive end point estimation values until convergence is reached.

Figure 3:
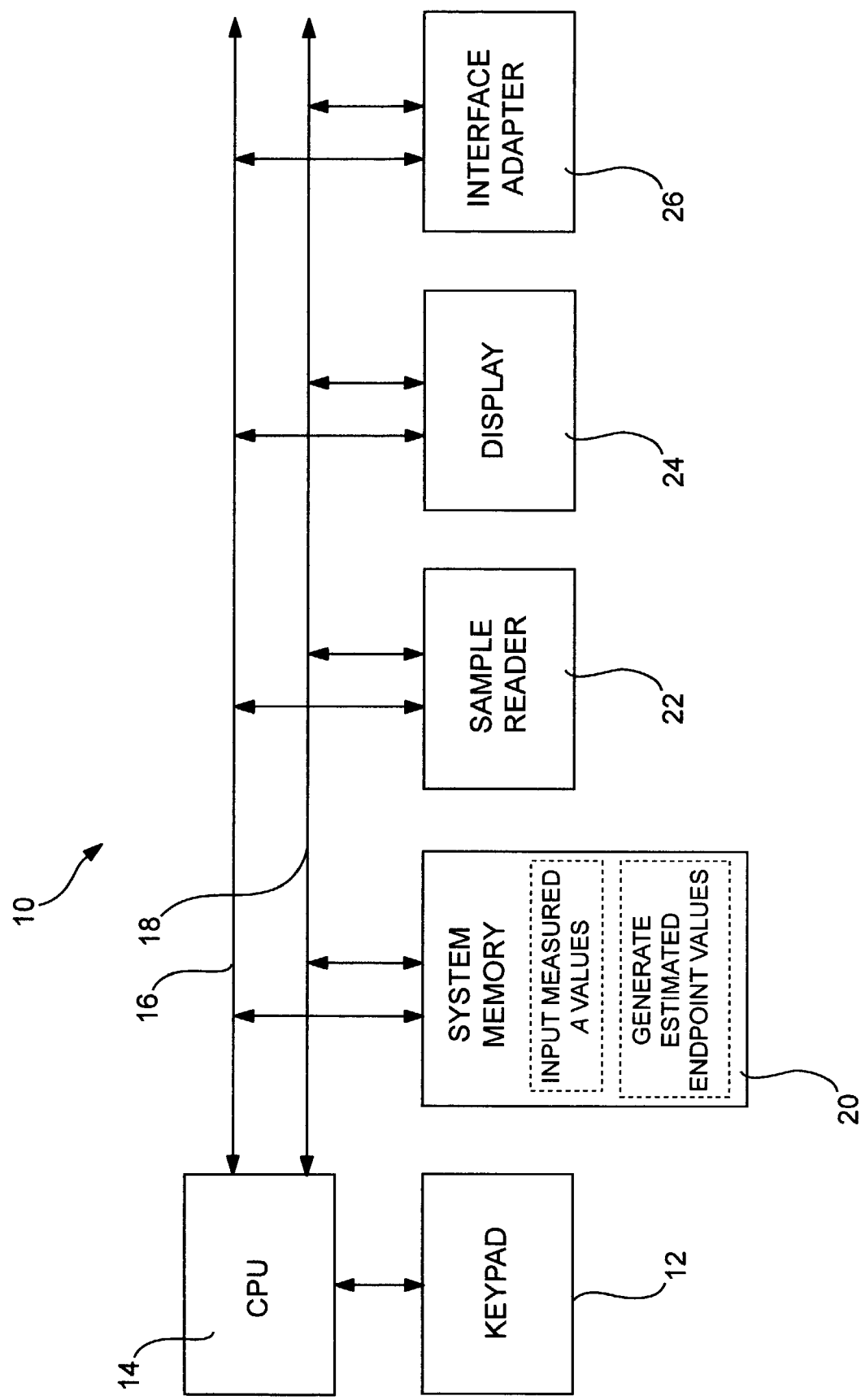
FIG. 3 is a schematic representation of a system usable for reaction end point determination in accordance with the present in vention.

Referring now to FIG. 3, a device or system 10 usable for reaction endpoint determination in accordance with the invention shown. The system 10 may comprise a hand held computer such as a personal digital assistant or "PDA". In other embodiments, data processing device may comprise a minicomputer, a microcomputer, a PC such as an INTEL® based processing computer or clone thereof, an APPLE® computer or clone thereof, a SUN® workstation, or other like computer. The system 10 includes a user interface element, shown in this embodiment as keypad 12, that is operatively coupled to a central processing unit or CPU 14.

CPU 14 is operatively coupled to components of system 10 via an address and data bus 16 and a control/status signal interface 18. These components include, inter alia, a system memory 20 which may comprise various memory elements (not shown) such as a DRAM primary or main memory, one or more SRAM buffers, and one or more read only memory elements in the form of ROM, PROM, EPROM, EEPROM or the like. System 10 also includes a sample reader 22 that is capable of measuring or detecting analyte levels in a sample. The system 10 may additionally include a display element 24 such as a CRT, LCD or other type of display, and an interface adapter 26 that allows the system 24 to interface with external data processors, sample readers or other external devices (not shown). Interface adapter 26 may be in the form of a GPIB, RS-232, PCI, USB, SCSI, ETHERNET®, FIREWIRE® or other IEEE 1394 interface. The CPU 14, memory 20, sample reader 22, display 24 and interface adapter 26 may be associated through a motherboard (not shown) in a conventional manner and interconnected thereon by address and data bus 16 and control/processing interface 18. System 10 may comprise various additional components (also not shown) such as a hard disk drive, floppy disk drive, NIC, CD drive, and/or other conventional hardware elements.

System memory 20 will generally contain a suitable operating system and software (not shown) suitable for the operation of the various hardware components, which are operatively coupled to memory 20 and CPU 14 via the address/data bus16 and control/status signal interface 18. Memory 20 also includes stored programming 28 that is capable of inputting or otherwise accepting at least three measurements, at three different time points, of a value associated with an observable indicative of progress of a reaction, and stored programming 30 that is capable of determining an end point value for the observable from the measurements as described above.

KITS

Also provided are kits for use in practicing the subject methods. The kits of the subject invention may comprise, for example, test strips or other sample holders containing an analyte or analytes, and a sample reader or meter for reading the test strips that contains logic configured to read or input a plurality of measured values from the test strips, apply the algorithm of equation (2) to the measured values, and output one or more end point estimation values according to the inputted measured values. The kits may further comprise printed instructions for application of a bodily fluid to the test strips, and use of the reader or meter for measuring values from the test strips.

EXAMPLES

The following examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed. Efforts have been made to ensure accuracy with respect to numbers used but some experimental errors and deviations should be accounted for. Unless indicated otherwise, parts are parts by weight, molecular weight is weight average molecular weight, temperature is in degrees Centigrade, and pressure is at or near atmospheric.

Example 1

End Point Determination For Colorimetric Blood Glucose Level Measurements

The following example demonstrates the usefulness of the method of the present invention for determining blood glucose levels of subjects and also compares the overall assay times (end point times) necessary to obtain reproducible results with conventional end point analysis methods.

In this example, the glucose monitor "SureStep®" was utilized to compare the assay time needed using the algorithm of the present invention with a conventional method of determining a subjects glucose levels. SureStep® is a blood glucose measuring system commercially available from Lifescan, Inc. of Milpitas, Calif. It comprises a handheld reflectance meter and a reagent strip utilizing an enzymatically catalyzed colorimetric chemistry (derivatives of MBTH and ANS, catalyzed by glucose oxidase and peroxidase). The chemistry is dispersed in a porous polysulfone membrane matrix, which absorbs the blood sample when the strip is used. The meter illuminates the reaction matrix with LED's having peak wavelengths of 660 and 940 nm. The 660 nm LED is used for detecting the product of the colorimetric reaction, which is proportional to the amount of glucose in the sample.

The meter takes reflectance measurements at one second intervals of the strip, then converts the reflectance values to the quantity K/S:

$$\frac{K}{S} = \frac{(1-R)^2}{2R} \quad (21)$$

where R is a quantity proportional to the ratio of amount of light scattered from the reaction matrix divided by the amount of light illuminating it. K/S is known in the art as a quantity which is approximately proportional to a light absorbing species (such as a dye) in a light scattering matrix such as a porous membrane. The meter collects the one second 660 nm K/S data ($K/S_{660}$) and processes it in 5 second windows which advance one second at a time. For each 5 second window, the slope (change in K/S per unit time) is computed, based on the change between the current K/S value and the one obtained 5 seconds earlier. When the reaction slows to the point where the slope is less than 1%/5 seconds, the endpoint is considered to have been reached. Glucose is calculated from the final K/S value according to the following equation:

$$\text{glucose} = -10 + 70.9 \cdot K/S_{660} - 2.86 \cdot K/S_{660}^2 - 0.277 \cdot K/S_{660}^2 \quad (22)$$

In this example, the K/S data calculated from the 660 nm reflectance were gathered at 1 second intervals for SureStep® at a range of temperatures between 15 and 35° C. Strips from seven production lots were employed, developed with spiked (contrived glucose level) whole blood at approximately normal hematocrit. Four blood samples were used for each temperature. The criteria employed for declaration of a projected endpoint were (1) that the reaction be greater than 50% complete and (2) three successive K/S estimates have a range of not more than 2% of the average K/S. If these criteria were not satisfied before the normal SureStep® endpoint (1% change in 5 seconds) was achieved, the SureStep® endpoint was used. Glucose was calculated according to the SureStep® relationship between K/S and glucose. SureStep® endpoint values were compared with the results of the new algorithm. At each temperature, the optimum $\Delta t$ was determined based on a combination of the root means squared (RMS) difference between SureStep® and this algorithm, and the observed reduction in average endpoint time. The data in Table 1 demonstrates the improvement in endpoint times, and the small magnitude of the typical disagreement between the results of the two algorithms.

TABLE 1

| Temperature ° C. | $\Delta t$ seconds | Ave. Assay Time with SureStep ®, sec. | Ave. Assay Time with Invention, sec. | RMS error (%) Invention vs SureStep ® |
|---|---|---|---|---|
| 15 | 5 | 41.7 | 16.7 | 2.2 |
| 20 | 4 | 29.1 | 12.9 | 1.7 |
| 25 | 3 | 31.9 | 15.5 | 2.1 |
| 30 | 2 | 18.2 | 10.4 | 1.0 |
| 35 | 1 | 12.4 | 8.4 | 1.0 |

While the present invention has been described with reference to the specific embodiments thereof, it should be understood by those skilled in the art that various changes may be made and equivalents may be substituted without departing from the true spirit and scope of the invention. In addition, many modifications may be made to adapt a particular situation, material, composition of matter, process, process step or steps, to the objective, spirit and scope of the present invention. All such modifications are intended to be within the scope of the claims appended hereto.

The invention claimed is:

1. A method for characterizing reaction end point, comprising:
    (a) initiating a chemical reaction including an observable A indicative of extent of reaction,
    (b) measuring first, second and third values $A_1$, $A_2$, and $A_3$ for said observable, at times $t_1$, $t_2$ and $t_3$ respectively wherein the time interval $t_2-t_1$ is substantially equal to the time interval $(t_3-t_2)$; and
    (c) determining an endpoint value $A_\infty$ for said observable according to the relationship $$A_\infty \cong A_2 - \frac{(A_3 - A_1)^2}{4(A_3 - 2A_2 + A_1)}.$$

2. The method of claim 1, wherein the chemical reaction comprises reaction with an oxidizable dye.

3. The method of claim 1, wherein said chemical reaction comprises an analyte obtained from a bodily fluid.

4. The method of claim 3, wherein said observable is associated with concentration of said analyte in a reaction sample.

5. The method of claim 1, wherein said observable comprises an optically detectable species associated with said chemical reaction.

6. The method of claim 1, wherein said observable comprises an electrically detectable species associated with said chemical reaction.

7. The method of claim 1, wherein said measuring comprises:
   (a) measuring a first set of values $A_1$, $A_2$, and $A_3$ for said observable during a first observation period; and
   (b) measuring a second set of values $A_1$, $A_2$, and $A_3$ for said observable during a second observation period.

8. The method of claim 7, wherein said determining comprises:
   (a) determining a first end point value from said first set of values;
   (b) determining a second end point value from said second set of values; and
   (c) determining a difference between said first and second end point values.

9. The method of claim 8, further comprising:
   (a) measuring an nth set of values $A_1$, $A_2$, and $A_3$ for said observable during an nth observation period;
   (b) determining an nth end point value from said nth set of values; and
   (c) determining if said first, second and nth end point values are convergent.

10. A system for characterizing a reaction end point, comprising:
   (a) stored programming capable of inputting first, second and third values $A_1$, $A_2$, and $A_3$ measured at times $t_1$, $t_2$ and $t_3$ respectively, for an observable associated with a chemical reaction and the time intervals $t_2-t_1$ and $t_3-t_2$ are substantially equal; and
   (b) stored programming capable of determining an endpoint value $A_\infty$ for said observable according to the relationship $$A_\infty \cong A_2 - \frac{(A_3 - A_1)^2}{4(A_3 - 2A_2 + A_1)}.$$

11. The system of claim 10, wherein the chemical reaction comprises reaction with an oxidizable dye.

12. The system of claim 10, wherein said chemical reaction comprises an analyte obtained from a bodily fluid.

13. The system of claim 12, wherein said observable is associated with concentration of said analyte in a reaction sample.

14. The system of claim 10, wherein said observable comprises an optically detectable species associated with said chemical reaction.

15. The system of claim 10, wherein said observable comprises an electrically detectable species associated with said chemical reaction.

16. The system of claim 10, further comprises:
   (a) stored programming capable of inputting a first set of values $A_1$, $A_2$, and $A_3$ for said observable during a first observation period; and
   (b) stored programming capable of inputting a second set of values $A_1$, $A_2$, and $A_3$ for said observable during a second observation period.

17. The system of claim 16, further comprises:
   (a) stored programming capable of determining a first end point value from said first set of values;
   (b) stored programming capable of determining a second end point value from said second set of values; and
   (c) stored programming capable of determining a difference between said first and second end point values.

18. The system of claim 17, further comprises:
   (a) stored programming capable of inputting an nth set of values $A_1$, $A_2$, and $A_3$ for said observable during an nth observation period;
   (b) stored programming capable of inputting an nth end point value from said nth set of values; and
   (c) stored programming capable of inputting if said first, second and nth end point values are convergent.

* * * * *